United States Patent
Clark et al.

(10) Patent No.: US 11,000,798 B1
(45) Date of Patent: May 11, 2021

(54) FIELD PROCESSING NATURAL GAS FOR SULFUR RECOVERY WITH DYNAMICALLY ADJUSTABLE FLOW RATE CONTROL

(71) Applicants: Billy G Clark, Dallas, TX (US); John C Bourdon, Peculiar, MO (US); Peter J Photos, El Campo, TX (US); Franklin Hailey Brown, II, San Antonio, TX (US); David Sisk, San Antonio, TX (US)

(72) Inventors: Billy G Clark, Dallas, TX (US); John C Bourdon, Peculiar, MO (US); Peter J Photos, El Campo, TX (US); Franklin Hailey Brown, II, San Antonio, TX (US); David Sisk, San Antonio, TX (US)

(73) Assignee: STREAMLINE INNOVATIONS, INC., San Antonio, TX (US)

( * ) Notice: Subject to any disclaimer, the term of this patent is extended or adjusted under 35 U.S.C. 154(b) by 0 days.

(21) Appl. No.: 16/425,270

(22) Filed: May 29, 2019

Related U.S. Application Data

(60) Provisional application No. 62/678,702, filed on May 31, 2018.

(51) Int. Cl.
| | | |
|---|---|---|
| B01D 53/52 | (2006.01) | |
| B01D 53/14 | (2006.01) | |
| B01J 8/00 | (2006.01) | |
| B01J 19/00 | (2006.01) | |
| G01N 33/00 | (2006.01) | |
| C01B 17/04 | (2006.01) | |
| C01B 17/05 | (2006.01) | |
| C10L 3/10 | (2006.01) | |
| G05B 19/05 | (2006.01) | |

(52) U.S. Cl.
CPC .......... *B01D 53/1468* (2013.01); *C01B 17/05* (2013.01); *C10L 3/103* (2013.01); *G01N 33/0044* (2013.01); *G05B 19/05* (2013.01); *B01D 2257/304* (2013.01)

(58) Field of Classification Search
None
See application file for complete search history.

(56) References Cited

U.S. PATENT DOCUMENTS

| | | | | |
|---|---|---|---|---|
| 2009/0092524 A1* | 4/2009 | Ravikumar | ........ | B01D 53/1462 422/171 |
| 2011/0033943 A1* | 2/2011 | Dessort | ................ | C01G 11/00 436/119 |

\* cited by examiner

*Primary Examiner* — Daniel Berns
(74) *Attorney, Agent, or Firm* — Anderson Gorecki LLP

(57) ABSTRACT

A dynamically adjustable rate sulfur recovery process continuously calculates and adjusts sour gas stream operating pressure and/or flow rate to maximize sweet gas output, thereby improving efficiency. A corresponding desulfurization system may include a fixed-sized pressure vessel, a flow control valve that controls the rate of flow of a sour gas stream into the pressure vessel, a sensor that measures sulfur concentration in the sour gas stream, a reagent tank, an oxidizer tank, and a phase separator that separates sweet gas as a gaseous phase after hydrogen sulfide in the sour gas stream in the pressure vessel is converted to elemental sulfur, sulfur species, or both by contact with reagent from the reagent tank and oxidizer from the oxidizer tank. A PLC (programmable logic controller) continuously calculates updated flow rates based on sulfur concentration measurements from the sensor to achieve maximum sweet gas production.

8 Claims, 2 Drawing Sheets

FIELD PROCESSING NATURAL GAS FOR SULFUR RECOVERY WITH DYNAMICALLY ADJUSTABLE FLOW RATE CONTROL

TECHNICAL FIELD

Aspects of the present disclosure are generally related to removing sulfur-based contaminants from raw natural gas streams.

BACKGROUND

Raw natural gas streams from oil wells, gas wells, and condensate wells include methane mixed with other hydrocarbons, e.g. ethane, propane, and butane, and other compounds and contaminants, e.g. water vapor, hydrogen sulfide ($H_2S$), carbon dioxide, helium, and nitrogen. Hydrogen sulfide is a highly toxic contaminant that should be removed by field processing at or near the well head. Desulfurization processes using aqueous sulfur reactants are known but require significant contact time which is problematic because reducing flow rate to achieve adequate contact time reduces the production rate. Further, the pressure is lowered when the flow rate is reduced so the gas stream must be re-pressurized after desulfurization.

SUMMARY

All examples, aspects, and features mentioned in this document can be combined in any technically possible way.

Some implementations include a method, in a system for desulfurization of a continuously flowing sour gas stream, comprising: continuously measuring sulfur concentration of the sour gas stream; continuously calculating updated flow rates based on measured sulfur concentration; and adjusting rate of flow of the sour gas stream into the pressure vessel based on the calculated updated flow rates. Some implementations comprise calculating a baseline flow rate to achieve adequate contact time with a reagent and oxidizer to produce a sweet gas stream based on pressure vessel size and geometry. Some implementations comprise calculating updated flow rates to achieve maximum flow within a constraint of adequate contact time with a reagent and oxidizer to produce a sweet gas stream. In some implementations continuously measuring sulfur concentration comprises measuring hydrogen sulfide concentration at time intervals of less than ten minutes. In some implementations continuously calculating updated flow rates based on measured sulfur concentration comprises calculating updated flow rates at time intervals of less than ten minutes. Some implementations comprise separating the sour gas stream into phases comprising a gaseous phase consisting of sweet gas. Some implementations comprise inputting reagent and oxidizer to the pressure vessel to convert hydrogen sulfide to elemental sulfur, sulfur species, or both. Some implementations comprise separating sweet gas as a gaseous phase after the hydrogen sulfide is converted to elemental sulfur, sulfur species, or both.

Some implementations include an apparatus comprising: a fixed-sized pressure vessel; a flow control valve that controls a rate of flow of a sour gas stream into the pressure vessel; a sensor that measures sulfur concentration in the sour gas stream; and a PLC (programmable logic controller) that: continuously calculates updated flow rates based on sulfur concentration measurements from the sensor; and adjusts rate of flow of the sour gas stream into the pressure vessel based on the calculated updated flow rates by sending control signals to the flow control valve, the flow control valve being responsive to the control signals to adjust the rate of flow of the sour gas stream into the pressure vessel. In some implementations the PLC calculates a baseline flow rate to achieve adequate contact time with a reagent and oxidizer to produce a sweet gas stream based on pressure vessel size and geometry. In some implementations the PLC calculates updated flow rates to achieve maximum natural gas flow with adequate contact time with a reagent and oxidizer to produce a sweet gas stream. In some implementations the sensor measures sulfur concentration at time intervals of less than ten minutes. In some implementations the PLC calculates updated flow rates at time intervals of less than ten minutes. In some implementations the pressure vessel comprises a contactor or a scrubbing unit containing an aqueous chemistry that interacts with the sour gas stream. Some implementations comprise at least one of: a triazine scavenger unit and an amine recovery unit. Some implementations comprise sources of reagent and oxidizer that are inputted to the pressure vessel to convert hydrogen sulfide to elemental sulfur, sulfur species, or both. Some implementations comprise a phase separator that separates sweet gas as a gaseous phase after the hydrogen sulfide is converted to elemental sulfur, sulfur species, or both.

Some implementations include an apparatus comprising: a fixed-sized pressure vessel; a flow control valve that controls a rate of flow of a sour gas stream into the pressure vessel; a sensor that measures sulfur concentration in the sour gas stream; a reagent tank; an oxidizer tank; a phase separator that separates sweet gas as a gaseous phase after hydrogen sulfide in a sour gas stream in the pressure vessel is converted to elemental sulfur, sulfur species, or both by contact with reagent from the reagent tank and oxidizer from the oxidizer tank; and a PLC (programmable logic controller) that: continuously calculates updated flow rates based on sulfur concentration measurements from the sensor to achieve maximum sweet gas production; and adjusts rate of flow of the sour gas stream into the pressure vessel based on the calculated updated flow rates by sending control signals to the flow control valve, the flow control valve being responsive to the control signals to adjust the rate of flow of the sour gas stream into the pressure vessel.

DETAILED DESCRIPTION

The presence of hydrogen sulfide in raw natural gas streams presents a challenge to small-scale hydrocarbon producers. Sour gas cannot be flared and requires costly piping systems to transport. Removal of hydrogen sulfide with current field processing technology is accomplished by lowering the pressure of the sour gas stream to achieve a reduced, constant flow rate, and thus extended contact time with a sulfur reactant including a margin of safety that is large enough to accommodate variability in the sulfur content of the stream. A dynamically adjustable rate sulfur recovery process continuously calculates and adjusts sour gas stream operating pressure and/or flow rate to maximize sweet gas output, thereby improving efficiency.

Figure 1:
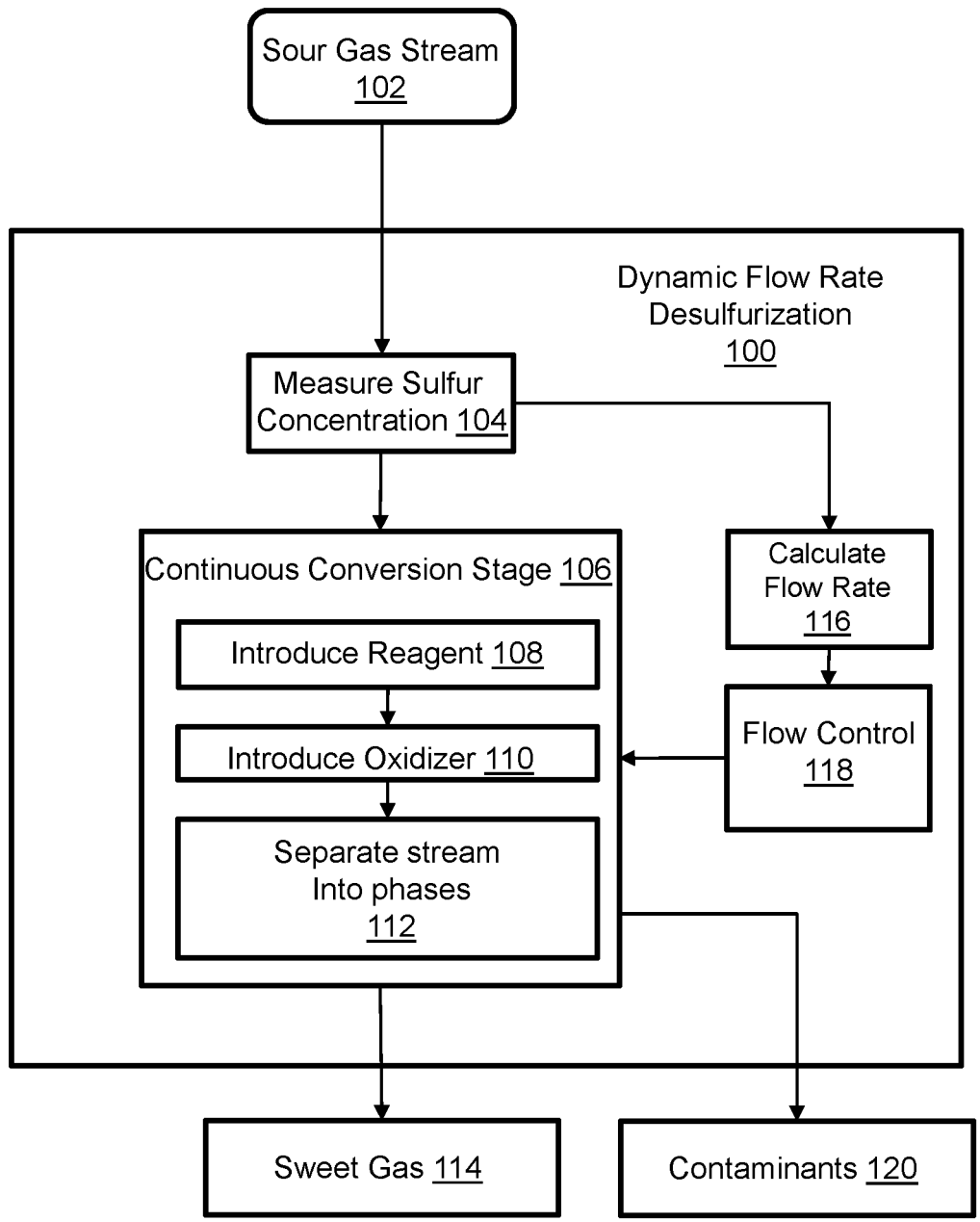
FIG. 1 illustrates an oxidation-reduction desulfurization process using dynamic flow rate control for improved efficiency.

FIG. 1 illustrates a dynamically adjustable flow rate desulfurization process 100 based on oxidation-reduction. A sour gas stream 102 is provided as input. The sour gas stream 102 may be raw natural gas or any other gas from any source, e.g. any type of well. Natural gas is usually considered sour if there are more than 5.7 milligrams of hydrogen sulfide per cubic meter of natural gas, which is equivalent to approximately 4 ppm by volume under standard temperature and pressure. For the purposes of the present disclosure a stream is considered desulfurized when it contains 30 parts per million or less of sulfur, by weight, in the aqueous phase. Step 104 is measuring the sulfur concentration in the sour gas stream. Measuring sulfur concentration may include measuring concentration of hydrogen sulfide specifically or measuring concentration of all sulfur-containing contaminants. The sour gas stream 102 is processed in a continuous conversion stage 106, which includes introducing reagent in step 108 and introducing oxidizer in step 110. The reagent may include one or more of ferric salts, ferrous salts, ferric chelants, ferrous chelants, and Fe-MGDA (ferric/ferrous methylglycinediacetate), e.g. Alanine, n,n-bid, (carboxymethyl) iron complex (CAS 547763-83-7). The oxidizer may include one or more of chlorine, hypochlorous acid, hypochlorite, chlorine dioxide, chlorite, perchlorate, inorganic peroxides, permanganates, sodium, oxygen, and ozone. The hydrogen sulfide in the sour gas stream is oxidized into elemental sulfur, sulfur species, or both by exposure to the combination of reagent and oxidizer. The stream is then separated into phases in step 112, with the gaseous phase being separated as sweet gas 114.

Dynamically adjustable flow rate control is based on continuously monitoring the sulfur concentration of the sour gas stream in step 104. In the present disclosure "continuously" includes uninterrupted analog measurements and signals as well as discrete analog or digital measurements, sampling, signals, and commands at intervals of no more than 10 minutes. Sulfur concentration measurement data is used to continuously calculate an updated flow rate in step 116. The updated flow rates are implemented in a flow control step 118. Specifically, the flow control step sets and adjusts the flow of sour gas into the continuous conversion stage 106. A baseline flow rate may be calculated in step 116 based on reactor vessel size and geometry. The baseline flow rate is then adjusted based on an initial measured sulfur concentration, and then continuously updated based on measured sulfur concentrations of the flowing sour gas stream. The flow rates are calculated to set a maximum flow rate within the constraint of achieving adequate contact time to produce the sweet gas 114, which is separated from other contaminants 120. The process is continuous and adjustments to changes in sulfur concentration are automatic. The required contact time is a function of reaction efficiency, the sulfur content of the sour gas stream, and reactor size as defined by cross-sectional area and height. The reaction efficiency may be a function of the selected reagent and oxidizer. Dynamic flow rate control enables automatic adjustment in response to fluctuations in the characteristics that effect the required contact time, which is an improvement relative to constant flow rate systems. Further, the contact time safety margin may be reduced or eliminated because the system dynamically responds to changing conditions rather than being statically configured for worst case conditions.

Figure 2:
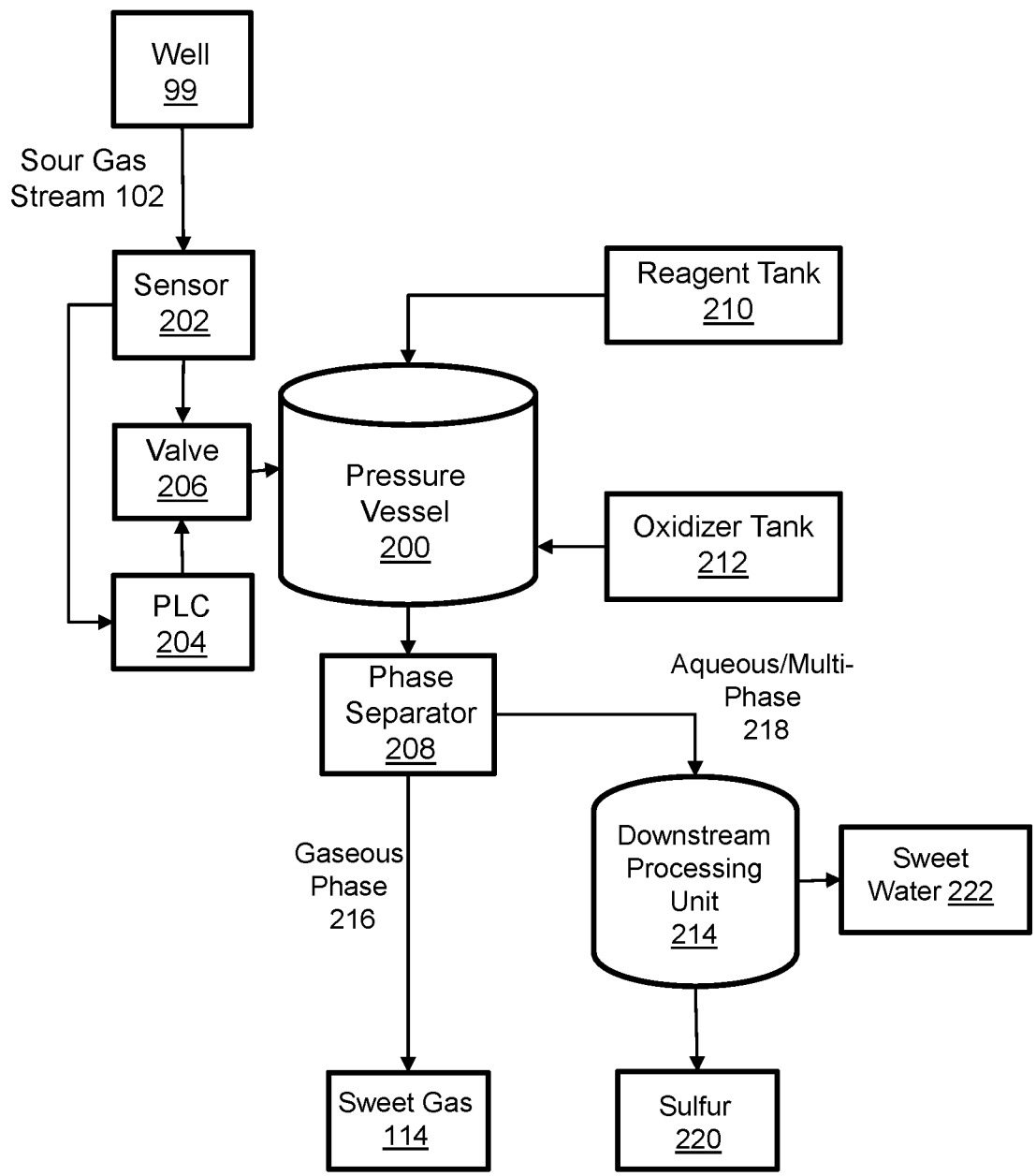
FIG. 2 illustrates an apparatus that implements the oxidation-reduction desulfurization process of FIG. 1.

FIG. 2 illustrates an apparatus for implementing the dynamically adjustable flow rate-controlled oxidation-reduction process of FIG. 1. The apparatus includes a pressure vessel 200, a sulfur concentration sensor 202, a PLC (programmable logic controller) 204, a flow control valve 206, a phase separator 208, a reagent tank 210, and an oxidizer tank 212. The sour gas stream 102 flows from a well 99 to the pressure vessel 200, e.g. at high pressure. The sensor 202 measures sulfur concentration in the sour gas stream 102. Sour gas, sulfur reagent, and oxidizer are introduced to the pressure vessel 200. The hydrogen sulfide in the sour gas stream is oxidized into elemental sulfur, sulfur species, or both by exposure to the reagent and oxidizer. The phase separator 208 separates the gaseous phase 216 as sweet gas 114. The remaining aqueous or multi-phase 218 is subjected to further processing by a downstream processing unit 214. The output of the downstream processing unit may include, but is not limited to, sulfur 220 (elemental sulfur, sulfur species, or both) and sweet water 222.

The sulfur concentration sensor 202 provides sulfur concentration measurement signals to the PLC 204. The PLC, which may include a wide variety of computing devices with non-transitory volatile memory, non-volatile storage, and processors, continuously calculates an updated optimal, maximum, or target sour gas stream flow rate based on the sulfur concentration measurements and reactor vessel characteristics to assure desulfurization (to a selected content) while providing maximum production of sweet gas. For example, a computer program on non-transitory memory in the PLC may calculate the minimal residence/contact time for the size and shape of the pressure vessel, set the flow rate based on the calculated residence/contact time, and make flow rate adjustments based on measurements from the sulfur concentration sensor. The PLC generates corresponding signals to actuate the control valve 206 to continuously regulate the flow rate of the sour gas stream into the pressure vessel. The commands sent from the PLC to the flow control valve cause the valve to restrict or increase the sour gas stream flow to achieve the calculated rate. Dynamically adjustable flow rate control helps to maintain the greatest possible pressure, which in turn minimizes reenergization costs for further transfer to downstream processes, such as pipelines and/or gathering stations.

In some embodiments the flow control valve 206 is upstream relative to the sulfur concentration sensor 202. Moreover, multiple flow control valves may be implemented, e.g. including valves upstream and downstream relative to the sulfur concentration sensor, pressure vessel, and/or phase separator.

Although dynamic flow control has been described in the context of continuous reaction oxidation-reduction with a sour gas stream, a wide variety of processes could be used. Consequently, a variety of fixed-sized pressure vessels such as a contactor or a scrubbing unit containing an aqueous chemistry that interacts with the natural gas stream could be used, e.g. a triazine scavenger unit, or an amine recovery unit.

Several features, aspects, embodiments, and implementations have been described. Nevertheless, it will be understood that a wide variety of modifications and combinations may be made without departing from the scope of the inventive concepts described herein. Accordingly, those modifications and combinations are within the scope of the following claims.

What is claimed is:
1. A method comprising:
   in a system for desulfurization of a continuously flowing sour gas stream in which sulfur concentration varies over time:

continuously measuring sulfur concentration of the sour gas stream with a sulfur concentration sensor that indicates a measured sulfur concentration;

continuously calculating updated flow rates based on the measured sulfur concentration with a computing device that is in communication with the sulfur concentration sensor; and dynamically adjusting rate of flow of the sour gas stream into a continuous conversion pressure vessel with a valve controlled by the computing device based on the continuously calculated updated flow rates to maintain continuous flow of the sour gas stream into the continuous conversion pressure vessel with adequate contact time with a reagent and oxidizer in the continuous conversion pressure vessel to produce a sweet gas stream from the sour gas stream.

2. The method of claim 1 comprising the computing device calculating a baseline flow rate to achieve adequate contact time with a reagent and oxidizer to produce a sweet gas stream based on pressure vessel size and geometry and controlling the valve to achieve the baseline flow rate.

3. The method of claim 1 comprising the computing device calculating updated flow rates to achieve maximum flow within a constraint of adequate contact time with a reagent and oxidizer to produce a sweet gas stream and controlling the valve to achieve the updated flow rates.

4. The method of claim 1 wherein continuously measuring sulfur concentration with a sulfur concentration sensor comprises measuring hydrogen sulfide concentration at time intervals of less than ten minutes.

5. The method of claim 1 wherein continuously calculating updated flow rates with the computing device based on measured sulfur concentration comprises calculating updated flow rates at time intervals of less than ten minutes.

6. The method of claim 1 comprising separating the sour gas stream into phases comprising a gaseous phase consisting of sweet gas.

7. The method of claim 1 comprising the computing device controlling inputting reagent and oxidizer to the pressure vessel to convert hydrogen sulfide to elemental sulfur, sulfur species, or both.

8. The method of claim 7 comprising separating sweet gas as a gaseous phase after the hydrogen sulfide is converted to elemental sulfur, sulfur species, or both.

\* \* \* \* \*